United States Patent [19]
Love et al.

[11] Patent Number: 6,096,720
[45] Date of Patent: Aug. 1, 2000

[54] LIPOSOMAL OLIGONUCLEOTIDE COMPOSITIONS

[75] Inventors: William Guy Love, Horsham; Paul Leslie Nicklin, Henfield, both of United Kingdom; Karen Ophelia Hamilton, Lawrence, Kans.; Judith Ann Phillips, Sevenoaks, United Kingdom

[73] Assignee: Novartis AG, Basel, Switzerland

[21] Appl. No.: 09/000,136

[22] PCT Filed: Jul. 24, 1996

[86] PCT No.: PCT/GB96/01775

§ 371 Date: Apr. 23, 1998

§ 102(e) Date: Apr. 23, 1998

[87] PCT Pub. No.: WO97/04787

PCT Pub. Date: Feb. 13, 1997

[30] Foreign Application Priority Data

Aug. 1, 1995 [GB] United Kingdom .................... 9515743
Sep. 19, 1995 [GB] United Kingdom .................... 9519130

[51] Int. Cl.[7] ......................... A61K 48/00; A61K 9/127; C12N 15/85; C07H 21/04
[52] U.S. Cl. ....................... 514/44; 424/450; 435/183; 435/194; 435/325; 435/366; 435/371; 435/375; 536/23.1; 536/24.31; 536/24.5
[58] Field of Search .......................... 424/450; 435/6, 435/69.1, 91.1, 440, 455, 458, 183, 194, 325, 354, 366, 371, 375; 514/44; 536/23.1, 24.3, 24.31, 24.33, 24.5

[56] References Cited

U.S. PATENT DOCUMENTS

| | | | |
|---|---|---|---|
| 5,034,506 | 7/1991 | Summerton et al. | 528/391 |
| 5,225,212 | 7/1993 | Martin et al. | 424/450 |
| 5,279,833 | 1/1994 | Rose | 424/450 |
| 5,354,853 | 10/1994 | Staveski et al. | 536/17.1 |
| 5,411,947 | 5/1995 | Hostetler et al. | 514/43 |
| 5,540,936 | 7/1996 | Coe et al. | 424/450 |
| 5,563,255 | 10/1996 | Monia et al. | 536/24.31 |

FOREIGN PATENT DOCUMENTS

| | | |
|---|---|---|
| 90/10448 | 9/1990 | WIPO . |
| 91/05545 | 5/1991 | WIPO . |
| 94/20073 | 9/1994 | WIPO . |
| 95/32987 | 12/1995 | WIPO . |

OTHER PUBLICATIONS

Woodle, M.C. Adavanced Drug Delivery Reviews vol. 16 (1995) pp. 249–265.
Science, vol. 254, p. 1497 (1991).

*Primary Examiner*—George C. Elliott
*Assistant Examiner*—Mark L. Shibuya
*Attorney, Agent, or Firm*—Myra H. McCormack; Henry P. Nowak

[57] ABSTRACT

A pharmaceutical composition comprising (A) an oligonucleotide 8 to 50 nucleotides in length, which is targeted to mRNA encoding human raf and is capable of inhibiting raf expression, entrapped in (B) sterically stabilized liposomes.

44 Claims, No Drawings

SEQUENCE LISTING

```
<160> NUMBER OF SEQ ID NOS: 25

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:
      oligonucleotide
<220> FEATURE:
<223> OTHER INFORMATION: phosphorothioate backbones
<220> FEATURE:
<223> OTHER INFORMATION: alternative oligonucleotide prepared with
      methoxy group substituting 2' sugar moiety

<400> SEQUENCE: 1
gctccattga tgcagcttaa                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:
      oligonucleotide
<220> FEATURE:
<223> OTHER INFORMATION: phosphorothioate backbone
<220> FEATURE:
<223> OTHER INFORMATION: alternative oligonucleotide having methoxy
      group subsituting for sugar moiety at 2' position

<400> SEQUENCE: 2
gatgcagctt aaacaattct                                              20

<210> SEQ ID NO 3
<211> LENGTH: 20
<212> TYPE: DNA
<213> ORGANISM: Artificial Sequence
<220> FEATURE:
```

```
<223> OTHER INFORMATION: Description of Artificial Sequence:
      oligonucleotide
<220> FEATURE:
<223> OTHER INFORMATION: phosphorotioate backbone
<220> FEATURE:
<223> OTHER INFORMATION: alternative oligonucleotide with uniform
      phosphorothiate backbone and nucleotides 1-7 and
      14-20 being substituted by methoxy at the 2'
      position of the sugar moiety
<220> FEATURE:
<223> OTHER INFORMATION: alternative oligonucleotide with uniform
      phosphorothiate backbone and nucleotides 1-6 and
      15-20 being substituted by methoxy at the 2'
      position of the sugar moiety
<220> FEATURE:
<223> OTHER INFORMATION: alternative oligonucleotide with uniform
      phosphorthiate backbone and nucleotides 1-5 and
      16-20 being substituted by methoxy at the 2 '
      position of the sugar moiety
<220> FEATURE:
<223> OTHER INFORMATION: alternative oligonucleotide with uniform
      phosphorothioate backbones and nucleotides 1-6 and
      15-20 being substituted at the 2' position of the
      sugar moiety by propoxy
<220> FEATURE:
<223> OTHER INFORMATION: alternative phosphorothioate backbones with
      nucleotides 1-6 and 15-20 substituted at the 2'
      position of the sugar moiety by fluoro
<220> FEATURE:
<223> OTHER INFORMATION: alternative oligonucleotide prepared with
      nucleotides 1-6 and 15-20 have phosphodiester
      backbone and 2'-propoxy substitutions
<220> FEATURE:
<223> OTHER INFORMATION: alternative oligonucleotide with nucleotides
      1-6 and 15-20 having phosphodiester backbones and
      2'-methoxyethoxy substitutents

<400> SEQUENCE: 3
tcccgcctgt gacatgcatt                                                   20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:
      oligonucleotide
<220> FEATURE:
<223> OTHER INFORMATION: phosphorothioate backbone

<400> SEQUENCE: 4
gtctggcgct gcaccactct                                                   20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial
      Sequence:oliigonucleotide
<220> FEATURE:
<223> OTHER INFORMATION: phosphorothioate backbone
<220> FEATURE:
<223> OTHER INFORMATION: alternative oligonucleotide having
      phosphodiester backbone and uniformly substituted by a propoxy
      group at the 2' position of the sugar moiety

<400> SEQUENCE: 5
cgctcctcct ccccgcggcg                                                   20

<210> SEQ ID NO 6
<211> LENGTH: 20
<212> TYPE: DNA
```

```
<213> ORGANISM: Artificial Sequence
<220> FEATURE:
<223> OTHER INFORMATION: Description of Artificial Sequence:
      oligonucleotide
<220> FEATURE:
<223> OTHER INFORMATION: phosphorothioate backbone
<220> FEATURE:
<223> OTHER INFORMATION: alternative oligonucleotide with uniform
      phosphorothiate backbones and nucleotides 1-11
      being substituted by methoxy at the 2' position of
      the sugar moiety

<400> SEQUENCE: 6
tcctcctccc cgcggcgggt                                                    20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:
      oligonucleotide
<220> FEATURE:
<223> OTHER INFORMATION: phosphorothioate backbone
<220> FEATURE:
<223> OTHER INFORMATION: alternative oligonucleotide with uniform
      phosphorothiate backbone with nucleotides 10-20
      being substituted by methoxy at the 2' position of
      the sugar moiety

<400> SEQUENCE: 7
ctcgcccgct cctcctcccc                                                    20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:
      oligonucleotide
<220> FEATURE:
<223> OTHER INFORMATION: alternative oligonucleotide with uniform
      phosphorothiotate backbones and nucleotides  7-20
      being substituted by methoxy at the 2' position of
      the sugar moiety

<400> SEQUENCE: 8
ctggcttctc ctcctcccct                                                    20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:
      oligonucleotide
<220> FEATURE:
<223> OTHER INFORMATION: phosphorothioate backbone
<220> FEATURE:
<223> OTHER INFORMATION: alternative oligonucleotide substituted at the
      2' position of the sugar moiety by a methoxy group
<220> FEATURE:
<223> OTHER INFORMATION: alternative oligonucleotide prepared with a
      phosphorothioate backbone and is uniformly
      substituted by fluoro at the 2' position of the
      sugar moiety

<400> SEQUENCE: 9
cgggaggcgg tcacattcgg                                                    20

<210> SEQ ID NO 10
```

```
<211> LENGTH: 20
<212> TYPE: DNA
<213> ORGANISM: Artificial Sequence
<220> FEATURE:
<223> OTHER INFORMATION: Description of Artificial Sequence:
      oligonucleotide
<220> FEATURE:
<223> OTHER INFORMATION: phosphorothioate backbone
<220> FEATURE:
<223> OTHER INFORMATION: alternative oligonucleotide includes uniform
      phosphorothiate backbone with nucleotides 8-15
      substituted by methoxy at the 2' position of the
      sugar moiety
<220> FEATURE:
<223> OTHER INFORMATION: alternative oligonucleotide prepared with
      uniform phosphorothioate backbones with nucleotides 8-20
      being substituted at the 2' position of the sugar
      moiety by flouro
<220> FEATURE:
<223> OTHER INFORMATION: alternative oligonucleotide having nucleotides
      8-20 phosphodiester backbones and 2'-propoxy
      substitutions

<400> SEQUENCE: 10
tctggcgctg caccactctc                                           20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:
      oligonucleotide
<220> FEATURE:
<223> OTHER INFORMATION: oligonucleotide has phosphorothiate backbones,
      nucleotides at positions 1-5 and 15-20 are
      substituted by methoxy at the 2' position of the
      sugar moiety

<400> SEQUENCE: 11
ttctcgcccg ctcctcctcc                                           20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:
      oligonucleotide
<220> FEATURE:
<223> OTHER INFORMATION: oligonucleotide has uniform phosphorothiate
      backbones, nucleotides 1-12 are substituted by
      methoxy at the 2' position of the sugar moiety

<400> SEQUENCE: 12
ttctcctcct cccctggcag                                           20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:
      oligonucleotide
<220> FEATURE:
<223> OTHER INFORMATION: oligonucleotide has uniform phosphorothiate
      backbone and nucleotides 10-20 are substituted by
      methoxy at the 2' position of the sugar moiety

<400> SEQUENCE: 13
cctgctggct tctcctcctc                                           20
```

-continued

```
<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 14
gtcaagatgg gctgaggtgg                                                    20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 15
ccatcccgga cagtcaccac                                                    20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 16
atgagctcct cgccatccag                                                    20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 17
aatgctggtg gaacttgtag                                                    20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 18
ccggtacccc aggttcttca                                                    20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 19
ctgggcagtc tgccgggcca                                                    20
```

```
<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 20
cacctcagct gccatccaca                                                    20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 21
gagattttgc tgaggtccgg                                                    20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial
      Sequence:oligionucleotide

<400> SEQUENCE: 22
gcactccgct caatcttggg                                                    20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 23
ctaaggcaca aggcgggctg                                                    20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 24
acgaacattg attggctggt                                                    20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 25 gtatcccccaa agccaagagg                                                   20
```

LIPOSOMAL OLIGONUCLEOTIDE COMPOSITIONS

This invention relates to liposomal oligonucleotide compositions, their preparation and their use.

Alterations in cellular genes which directly or indirectly control cell growth and differentiation are considered to be the main cause of cancer. There are some thirty families of genes, called oncogenes, which are implicated in human tumor formation. Members of one such family, the raf gene family, are frequently found to be mutated in human tumors. The raf family includes three highly conserved genes termed A-, B- and c-raf (also called raf-1). c-Raf, the best characterized member of the raf family, is the cellular homologue of v-raf, the transforming gene of the murine sarcoma virus 3611. Raf genes encode protein kinases that are thought to play important regulatory roles in signal transduction processes that regulate cell proliferation. Mutation of raf genes causing a truncation or other modification that leads to the expression of raf kinase without a functional negative regulatory domain at the amino-terminal end results in conversion to a form which is implicated in transformation of mammalian cells in culture, and tumor formation. A raf gene having an absent or inactive regulatory domain is said to be "activated." Activated (truncated) raf has been detected in a variety of human cancers including small-cell lung carcinoma, primary stomach cancer, renal cancer, breast cancer, laryngeal cancer, skin fibroblasts from members of a cancer-prone family (Li-Fraumeni syndrome), and in a human glioblastoma cell line. Abnormal expression of the normal (non-activated) c-raf protein is believed to play a role in abnormal cell proliferation since it has been reported that 60% of all lung carcinoma cell lines express unusually high levels of normal c-raf mRNA and protein. Rapp et al., The Oncogene Handbook, E. P. Reddy, A. M. Skalka and T. Curran, eds., Elsevier Science Publishers, New York, 1988, pp. 213–253.

Oligonucleotides have been employed as therapeutic moieties in the treatment of disease states in animals and man. For example, there have been identified antisense, triplex and other oligonucleotide compositions which are capable of modulating expression of genes implicated in viral, fungal and metabolic diseases. There remains a need for compositions which can effectively inhibit abnormal raf gene expression, i.e. inhibit expression of the activated raf product or inhibit unusually high level of expression of the normal raf product.

It has now been found that compositions which inhibit abnormal gene expression and retain high anti-hyperproliferative activity after prolonged circulation in the bloodstream can be prepared by formulation of oligonucleotides capable of inhibiting raf expression which are targeted to mRNA encoding human raf within sterically stabilised liposomes. These compositions facilitate the reduction of accumulation of oligonucleotide in non-target organs and reduction of acute and chronic side effects during prolonged treatment.

Accordingly, the present invention provides a pharmaceutical composition comprising (A) an oligonucleotide 8 to 50 nucleotides in length, which is targeted to mRNA encoding human raf and is capable of inhibiting raf expression, entrapped in (B) sterically stabilised liposomes.

The relationship between an oligonucleotide and its complementary nucleic acid target to which it hybridises is commonly referred to as "antisense". Targetting an oligonucleotide to a chosen nucleic acid target may involve a multistep process. The process usually begins with identifying a nucleic acid sequence whose function is to be modulated. This may be, as examples, a cellular gene (or mRNA made from the gene) whose expression is associated with a particular disease state, or a foreign nucleic acid from an infectious agent. In the present invention, the target is a nucleic acid encoding raf; in other words, the raf gene or mRNA expressed from the raf gene. The targeting process also includes determination of a site or sites within the nucleic acid sequence for the oligonucleotide interaction to occur such that the desired effect—inhibition of abnormal raf gene expression-will result. Once the target site or sites have been identified, oligonucleotides are chosen which are sufficiently complementary to the target, i.e., hybridize sufficiently well and with sufficient specificity, to give the desired inhibition.

Inhibition of abnormal raf gene expression can be measured in ways which are routine in the art, for example by Northern blot assay of mRNA expression or Western blot assay of protein expression. Effects on cell proliferation or tumor cell growth can also be measured, as described hereinafter in the Examples. "Hybridization," in the context of this invention, means hydrogen bonding, also known as Watson-Crick base pairing, between complementary bases, usually on opposite nucleic acid strands or two regions of a nucleic acid strand. Guanine and cytosine are examples of complementary bases which ar e known to form three hydrogen bonds between them. Adenine and thymine are examples of complementary bases which form two hydrogen bonds between them. "Specifically hybridizable" and "complementary" are terms which are used to indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment, or, in the case of in vitro assays, under conditions in which the assays are conducted.

In preferred embodiments of this invention, the oligonucleotide (A) is targeted to mRNA encoding c-raf or A-raf. In accordance with this invention, persons of ordinary skill in the art will understand that mRNA includes not only the coding region which carries the information to encode a protein using the three letter genetic code, but also associated ribonucleotides which form a region known to such persons as the 5'-untranslated region, the 3'-untranslated region, the 5' cap region, intron regions and intron/exon or splice junction ribonucleotides. Thus, oligonucleotides may be formulated in accordance with this invention which are targeted wholly or in part to these associated ribonucleotides as well as to the coding ribonucleotides. In preferred embodiments, the oligonucleotide is targeted to a translation initiation site (AUG codon) or sequences in the 5'- or 3'-untransiated region of th e human c-raf mRNA. Th e functions of messen ger RNA to be interfered with include all vital functions such as translocation of the RNA to the site for protein translation, actual translation of protein from the RNA, splicing or maturation of the RNA and possibly even independent catalytic activity which may be engaged in by the RNA. The overall effect of such interference with the RNA function is to cause interference with raf protein expression. Oligonucleotides targeted to mRNA encoding human A-raf and, especially, human c-raf are presently preferred; however, compositions for modulating expression of other forms of raf are also believed to have utility and are comprehended by this invention.

In the context of this invention, the term "oligonucleotide" refers to an oligomer or polymer of nucleotide or nucleoside monomers consisting of naturally occurring bases, sugars and intersugar (backbone) linkages. The term "oligonucleotide" also includes oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases.

In some preferred oligonucleotides (A), at least one nucleotide is modified at the 2' position of the sugar moiety. Certain preferred oligonucleotides (A) are chimeric oligonucleotides. "Chimeric oligonucleotides" or "chimeras", in the context of this invention, are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the RNA target) and a region that is a substrate for RNase H cleavage. In one preferred embodiment, a chimeric oligonucleotide comprises at least one region modified to increase target binding affinity, and usually, a region that acts as a substrate for RNAse H. Affinity of an oligonucleotide for its target (in this case a nucleic acid encoding raf) is routinely determined by measuring the Tm of an oligonucleotide/target pair, which is the temperature at which the oligonucleotide and target dissociate; dissociation is detected spectrophotometrically. The higher the Tm, the greater the affinity of the oligonucleotide for the target. In a more preferred embodiment, the region of the oligonucleotide which is modified to increase raf mRNA binding affinity comprises at least one nucleotide modified at the 2' position of the sugar, particularly a 2'-alkoxy, 2'-alkoxyalkoxy or 2'-fluoro-modified nucleotide. Such modifications are routinely incorporated into oligonucleotides and these oligonucleotides have been shown to have a higher Tm (i.e., higher target binding affinity) than 2'-deoxyoligonucleotides against a given target. The effect of such increased affinity is to greatly enhance antisense oligonucleotide inhibition of raf gene expression. RNAse H is a cellular endonuclease that cleaves the RNA strand of RNA:DNA duplexes; activation of this enzyme therefore results in cleavage of the RNA target, and thus can greatly enhance the efficiency of antisense inhibition. Cleavage of the RNA target can be routinely demonstrated by gel electrophoresis. In another preferred embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. Oligonucleotides which contain at least one phosphorothioate modification are presently more preferred. In some cases, oligonucleotide modifications which enhance target binding affinity are also, independently, able to enhance nuclease resistance.

Specific examples of some preferred oligonucleotides may contain phosphorothioate phosphotriester, methyl phosphonate, short chain alkyl or cycloalkyl intersugar linkages or short chain heteroatomic or heterocyclic intersugar ("backbone") linkages. Most preferred are phosphorothioates and those with $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—P—O—$CH_2$). Also preferred are oligonucleotides having morpholino backbone structures, for example as described in U.S. Pat. No. 5,034,506. In other preferred embodiments, such as the protein-nucleic acid or peptide-nucleic acid (PNA) backbone, the phosphodiester backbone of the oligonucleotide may be replaced with a polyamide backbone, the bases being bound directly or indirectly to the aza nitrogen atoms of the polyamide backbone, as described by P. E. Nielsen, M. Egholm, R. H. Berg, O. Buchardt, Science 1991, 254, 1497. Other preferred oligonucleotides may contain alkyl and halogen-substituted sugar moieties comprising one of the following at the 2' position: OH, SH, $SCH_3$, F, OCN, $OCH_2OCH_3$, $OCH_2CH_2OCH_3$, $OCH_2O(CH_2)_nCH_3$, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O—, S—, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a cholesteryl group; a conjugate; a reporter group; an intercalator; a group for improving the pharmacokinetic properties of an oligonucleotide; or a group for improving the pharmacodynamic properties of an oligonucleotide and other substituents having similar properties. Oligonucleotides may also have sugar mimetics such as cyclobutyls in place of the pentofuranosyl group. Other preferred embodiments may include at least one modified base form or "universal base" such as inosine.

In certain especially preferred embodiments of the invention, all nucleotides of the oligonucleotide (A) are 2'-deoxynucleotides and all backbone linkages are phosphorothioate linkages.

In certain other especially preferred embodiments, the oligonucleotide (A) is a chimeric oligonucleotide having one or more regions with 2'-deoxynucleotides and one or more regions with 2'-alkoxyalkoxynucleotides, particularly 2'-methoxyethoxynucleotides, the one or more, 2'-deoxynucleotide regions preferably having phosphorothioate backbone linkages and the one or more 2'-alkoxyalkoxynucleotide regions preferably having phosphodiester backbone linkages. These chimeric oligonucleotides preferably comprise a region of 2'-deoxynucleotides between two regions of 2'-alkoxyalkoxynucleotides.

The oligonucleotides used as component (A) of the composition of the invention may be conveniently and routinely made using well-known techniques such as solid phase synthesis. Equipment for such synthesis is available commercially from various sources including Applied Biosystems. The use of such techniques to prepare oligonucleotides such as the phosphorothioates and alkylated derivatives is well known. It is also well known to use similar techniques and commercially available modified amidites and controlled-pore glass (CPG) products such as biotin, fluorescein, acridine or psoralen-modified amidites and/or CPG (available from Glen Research, Sterling VA) to synthesize fluorescently labeled, biotinylated or other modified oligonucleotides such as cholesterol-modified oligonucleotides.

Specific especially preferred oligonucleotides, for which the nucleotide sequences have been published in WO 95/32987, include the following:

| No. | Sequence (5' → 3') | Site | SEQ ID NO: |
|---|---|---|---|
| ON1 | GCTCCATTGATGCAGCTTAA | AUG | 1 |
| ON2 | GATGCAGCTTAAACAATTCT | 5'UTR | 2 |
| ON3 | TCCCGCCTGTGACATGCATT | 3'UTR | 3 |
| ON4 | GTCTGGCGCTGCACCACTCT | 3'UTR | 4 |
| ON5 | CGCTCCTCCTCCCCGCGGCG | 5'UTR | 5 |
| ON6 | TCCTCCTCCCCGCGGCGGGT | 5'UTR | 6 |
| ON7 | CTCGCCCGCTCCTCCTCCCC | 5'UTR | 7 |
| ON8 | CTGGCTTCTCCTCCTCCCCT | 3'UTR | 8 |
| ON9 | CGGGAGGCGGTCACATTCGG | 5'UTR | 9 |
| ON10 | TCTGGCGCTGCACCACTCTC | 3'UTR | 10 |

ON1 to ON10 are oligodeoxynucleotides with phosphorothioate backbones desgined using the Genbank c-raf sequence HUMRAFR (Genbank listing x 03484), synthesised and tested for inhibition of c-raf mRNA expression in T24 bladder carcinoma cells using a Northern blot assay.

Other specific especially preferred oligonucleotides include:

| No. | Sequence | Site | SEQ ID NO: |
|---|---|---|---|
| ON11 | CGGGAGGCGGTCACATTCGG | 5'UTR | 9 |
| ON12 | GATGCAGCTTAAACAATTCT | 5'UTR | 2 |
| ON13 | GCTCCATTGATGCAGCTTAA | AUG | 1 |
| ON14 | CGCTCCTCCTCCCCGCGGCG | 5'UTR | 5 |
| ON15 | CGGGAGGCGGTCACATTCGG | 5'UTR | 9 |

ON11, ON12 and ON13 are oligonucleotides synthesised with phosphorothioate backbones and uniformly substituted at the 2' position of the sugar moiety by a methoxy group. ON14 is synthesized with a phosphodiester backbone and is uniformly substituted by a propoxy group at the 2' position of the sugar moiety. ON15 is synthesized with a phosphorothioate backbone and is uniformly substituted by fluoro at the 2' position of the sugar moiety.

Specifically especially preferred chimeric oligonucleotides include:

| No. | Sequence | Target Site | SEQ ID NO: |
|---|---|---|---|
| ON16 | TCCTCCTCCCCGCGGCGGGT | 5'UTR | 6 |
| ON17 | CTCGCCCGCTCCTCCTCCCC | 5'UTR | 7 |
| ON18 | TTCTCGCCCGCTCCTCCTCC | 5'UTR | 11 |
| ON19 | TTCTCCTCCTCCCCTGGCAG | 3'UTR | 12 |
| ON20 | CTGGCTTCTCCTCCTCCCCT | 3'UTR | 8 |
| ON21 | CCTGCTGGCTTCTCCTCCTC | 3'UTR | 13 |
| ON22 | TCCCGCCTGTGACATGCATT | 3'UTR | 3 |
| ON23 | TCCCGCCTGTGACATGCATT | 3'UTR | 3 |
| ON24 | TCCCGCCTGTGACATGCATT | 3'UTR | 3 |
| ON25 | TCTGGCGCTGCACCACTCTC | 3'UTR | 10 |

ON16 to ON25 are chimeric oligonucleotides with uniform phosphorothiate backbones, the nucleotides shown underlined being substituted by methoxy at the 2' position of the sugar moiety.

Other specific especially preferred chimeric oligonucleotides include:

| No. | Sequence | Target Site | SEQ ID NO: |
|---|---|---|---|
| ON26 | TCCCGCCTGTGACATGCATT | 3'UTR | 3 |
| ON27 | TCCCGCCTGTGACATGCATT | 3'UTR | 3 |
| ON28 | TCTGGCGCTGCACCACTCTC | 3'UTR | 10 |

ON26, ON27 and ON28 are chimeric oligonucleotides with uniform phosphorothioate backbones, the nucleotides shown underlined being substituted at the 2' position of the sugar moiety, in ON26 by propoxy and in ON27 and ON28 by fluoro.

Specific preferred chimeric oligonucleotides with 2' modifications and chimeric phosphorothiote/phosphodiester backbones include:

| No. | Sequence | Target Site | SEQ ID NO: |
|---|---|---|---|
| ON29 | TCCCGCCTGTGACATGCATT | 3'UTR | 3 |
| ON30 | TCTGGCGCTGCACCACTCTC | 3'UTR | 10 |
| ON31 | TCCCGCCTGTGACATGCATT | 3'UTR | 3 |

ON29 and ON30 have regions, shown underlined, which have both 2'-propoxy substituents and phosphodiester backbones. ON31 has regions, shown underlined, which have both 2'-methoxyethoxy substituents and phosphodiester backbones.

It is believed that certain oligonucleotides targeted to portions of the A-raf mRNA and which inhibit A-raf expression will be useful for interfering with cell hyperproliferation.

Specific phosphorthioate deoxyoligonucleotides of this kind, designed and synthesised using the Genbank A-raf sequence HUMARAFIR (Genbank listing x 04790), for which the nucleotide sequences have been published in WO 95/32987, include the following:

| No. | Sequence | Target Site | SEQ ID NO: |
|---|---|---|---|
| ON32 | CCA TCC CGG ACA GTC ACC AC | Coding | 15 |
| ON33 | ATG AGC TCC TCG CCA TCC AG | Coding | 16 |
| ON34 | AAT GCT GGT GGA ACT TGT AG | Coding | 17 |
| ON35 | CCG GTA CCC CAG GTT CTT CA | Coding | 18 |
| ON36 | CTG GGC AGT CTG CCG GGC CA | Coding | 19 |
| ON37 | CAC CTC AGC TGC CAT CCA CA | Coding | 20 |
| ON38 | GAG ATT TTG CTG AGG TCC GG | Coding | 21 |
| ON39 | GCA CTC CGC TCA ATC TTG GG | Coding | 22 |
| ON40 | CTA AGG CAC AAG GCG GGC TG | Stop | 23 |
| ON41 | ACG AAC ATT GAT TGG CTG GT | 3'UTR | 24 |
| ON42 | GTA TCC CCA AAG CCA AGA GG | 3'UTR | 25 |
| ON43 | GTC AAG ATG GGC TGA GGT GG | 5'UTR | 14 |

In compositions of the invention, the oligonucleotide (A) is entrapped in sterically stabilised liposomes (B). Examples of sterically stabilised liposomes are those in which part of the lipid is a glycolipid, particularly ganglioside GM, saturated phosphatidylinositol or galactocerebroside sulphate ester, such as those described in WO 88/04924; those in which part of the lipid is derivatised with hydrophilic polymer such as those described in WO 91/05545 or U.S. Pat. No. 5,225,212; and those comprising a vesicle-forming lipid and a lipid-polymer conjugate having a hydrophobic moiety and a polar head group, such as those described in WO 94/20073.

In a preferred embodiment of the invention, the liposomes (B) comprise at least one underivatised vesicle-forming lipid and at least one vesicle-forming lipid derivatised with hydrophilic polymer which may be, for example, a polymer containing a hydroxy and/or carboxyl group such as a polylactic acid, a polyglycolic acid or, preferably, a polyethylene glycol. More preferably, the hydrophilic polymer is a polyethyleneglycol having a molecular weight of 1000 to 5000 daltons, such as 1500 to 2500 daltons, especially 1800 to 2200 daltons. The hydrophilic polymer is preferably derivatised with a polar head group of a phospholipid, especially a phospholipid having an amino head group, i.e. the derivatised lipid is preferably a phospholipid having an amino group, especially a phosphatidylethanolamine such as dilauroyl phosphatidylethanolamine, dimyristoyl phosphatidylethanolamine, dioleoyl phosphatidylethanolamine or, particularly, distearoyl phosphatidylethanolamine.

Various methods of derivatising an amino-containing lipid with a hydroxyl- and/or carboxyl-containing hydrophilic polymer will be apparent to those skilled in the art. Several such methods are described in WO 91/05545 and U.S. Pat. No. 5,225,212; the phospholipid having an amino group may be derivatised with the hydrophilic polymer by any of these methods. Preferably, the phospholipid having an amino group is derivatised with a hydroxyl-containing hydrophilic polymer such that the polymer is attached to the phospholipid through a carbamate linkage; this may be achieved by reacting a hydroxyl group of the polymer (other hydroxyl groups being capped, if necessary in view of their reactivity, for example by etherification) with diimidazole to give an activated imidazole—terminated polymer which is then reacted with the amino-containing phospholipid to couple the phospholipid to the hydrophilic polymer through a carbamate group, as described in WO 91/05545 or U.S. Pat. No. 5,225,212. In an especially preferred embodiment of the invention, the derivatised lipid is an amino-containing phospholipid, particularly a phosphatidylethanolamine, coupled through a carbamate group to a polyethyleneglycol capped at one end by an alkoxy group, particularly a methoxy or ethoxy group. Such a derivatised lipid is available commercially.

The derivatised lipid is generally present in a minor molar amount relative to the total Lipid content of the liposomes, preferably in an amount of 1 to 20 mole % of the total lipid content, although a lower amount, for example 0.1 mole %, may be appropriate when the derivatised lipid has a high molecular weight. The major part of the lipid content of the liposomes generally comprises one or more underivatised vesicle-forming lipids such as are used in conventional liposomes. Such lipids include, for example, lipids having two hydrocarbon chains, usually in acyl groups, and a polar head group, including phospholipids, for example phosphatidylcholines such as dilauroyl phosphatidylcholine, dimyristoyl phosphatidylcholine, dipalmitoyl phosphatidylcholine, distearoyl phosphatidylcholine, dioleoyl phosphatidylcholine, dilinoleoyl phosphatidylcholine, 1-palmitoyl-2-oleoyl phosphatidylcholine, phosphatidylethanolamines such as those mentioned hereinbefore, and phosphatidic acids such as dimyristoyl phosphatidic acid and dipalmitoyl phosphatidic acid. Other conventionally used lipids include sterols, particularly cholesterol, and glycolipids such as those mentioned hereinbefore. Preferably, the underivatised lipid comprises a mixture of a phospholipid, especially a phosphatidylcholine, and a sterol, especially cholesterol.

In the abovementioned preferred embodiment, the sterically stabilised liposomes (B) preferably comprise 4–10 mol % of the derivatised lipid, 40–80 mol % of the underivatised phospholipid and 20–50 mol % of the sterol. In especially preferred liposomes (B), the molar ratio of derivatised lipid: underivatised phospholipid: sterol is 1:10:5.

In another preferred embodiment of the invention, the liposomes (B) comprise (i) a glycolipid together with (ii) a vesicle-forming phospholipid or sphingolipid or mixture thereof and, optionally, (iii) a sterol and/or an acylglycerol lipid. The glycolipid is preferably a negatively charged glycolipid, especially ganglioside $GM_1$ (monosialoganglioside) or hydrogenated phosphatidylinositol. The vesicle-forming phospholipid may be one or more of the phospholipids hereinbefore mentioned, preferably a phosphatidylcholine, a phosphatidylethanolamine or a mixture thereof. Especially preferred phospholipids are distearoyl phosphatidylcholine and dioleoyl phosphatidylethanolamine. The sphingolipid is preferably sphingomyelin and is preferably used together with a phospholipid. The sterol may be, for example, ergosterol or, preferably, cholesterol. The acylglycerol lipid may be an ester of glycerol containing two fatty acid acyl groups each having at least 12 carbon atoms, for example lauroyl, myristoyl, palmitoyl or oleoyl groups, and one acyl group of formula $R^1CO$—, where $R^1$ is a residue, containing up to 10 carbon atoms, of a monocarboxylic acid of formula $R^1COOH$ after removal of the —COOH group or, preferably, of formula —$COR^2COOH$ where $R^2$ is a residue, containing up to 10 carbon atoms, preferably 1 to 4 carbon atoms, of a dicarboxylic acid of formula HOOC—$R^2$—COOH, especially succinic acid, after removal of both —COOH groups. An especially preferred acylglycerol is 1,2-dipalmitoyl-sn-3-succinyl glycerol.

In this second preferred embodiment of the invention, the liposomes preferably comprise (i) a negatively charged glycolipid together with (ii) a vesicle-forming phospholipid and/or sphingolipid and (iii) a sterol or acylglycerol lipid, especially (i) ganglioside $GM_1$ or hydrogenated phosphatidylinositol together with (ii) distearoyl phosphatidylcholine or dioleoyl phosphatidylethanolamine or a mixture thereof with sphingomyelin and (iii) cholesterol or 1,2-dipalmitoyl-sn-3-succinylglycerol.

The liposomes may comprise from 2 to 20 mol% of the glycolipid (i) and 80 to 98 mol% of (ii) the phospholipid, sphingolipid or mixture thereof. In preferred embodiments, where the liposomes also comprise a sterol or acylglycerol, they may comprise 2 to 20 mol %, preferably 4 to 10 mol %, of the glycolipid, 40 to 80 mol %, preferably 60 to 80 mol %, of the phospholipid, sphingolipid or mixture thereof and 10 to 50 mol %, preferably 20 to 40 mol%, of the sterol or 5 to 40 mol %, preferably 10 to 30 mol %, of the acylglycerol.

Specific especially preferred liposomes (B) are those described hereinafter in the Examples.

The oligonucleotide-containing liposomes of the invention can be prepared using known methods for the preparation of drug-containing liposomes. For example, in one method, the lipid composition is dissolved in an organic solvent, such as an alcohol, ether, halohydrocarbon or mixture thereof, the solvent is removed from the resulting solution, for example by rotary evaporation or freeze drying, and the resulting lipid film is hydrated by dispersing in an aqueous medium, such as phosphate-buffered saline or an aqueous solution of a sugar, e.g. lactose, which medium also contains the oligonucleotide (A), to give an aqueous suspension of liposomes in the form of multilamellar vesicles (MLV's). The aqueous liposome suspension may be treated to reduce the liposome size, for example to give small unilamellar vesicles (SUV's), using known methods, for example by sonication or by extrusion through one or more membranes, e.g. polycarbonate membranes, having a selected pore size. Liposomes according to the invention preferably have on average a particle size below 500 nm, more preferably 50 to 200 nm, especially 80 to 120 nm.

It is generally desirable to have as high a weight ratio of oligonucleotide to lipid as possible consistent with liposome stability. The maximum for this weight ratio may vary depending on the nature and composition of the lipid component, but in general this maximum is likely to be about 1:20. Ratios between 1:40 and 1:400 can be used with good results.

The invention includes a method of inhibiting the expression of human raf which comprises contacting tissues or cells which express human raf with a composition of the invention as hereinbefore defined. The invention also includes a method of treating mammalian cancer which comprises administering a composition of the invention as hereinbefore defined to a mammal, particularly a human, in need of such treatment.

The composition of the invention may be administered by pulmonary delivery or, preferably, parenterally, for example intravenously, subcutaneously, intraperitoneally or intramuscularly. The dosage depends principally on the method of administration and on the severity and responsiveness of the condition to be treated. Individual doses and the administration regime can best be determined by individual judgement of a particular case of illness. Diseases which may be treated with the composition include mammalian cancer, particularly human cancer such as lung cancer, stomach cancer, renal cancer, breast cancer, laryngeal cancer, pancreatic cancer, colorectal cancer and malignant melanoma.

The invention is illustrated by the following Examples.

EXAMPLE 1

A derivatised lipid, prepared by coupling distearoyl phosphatidylethanolamine to a methoxy-capped polyethylene glycol of molecular weight 2000 through a carbamate group (DSPE-MPEG 2000 available from Genzyme), distearoyl phosphatidylcholine (available from Sigma Chemical) and cholesterol are dissolved, at a molar ratio of 1:10:5, in chloroform. The solvent is removed by rotary evaporation to leave a lipid film. This film (250 mg) is hydrated with Hanks' balanced salt solution (2 ml) buffered to pH 7.4 with 25 mM 4-(2-hydroxyethyl)piperazine-1-ethane sulphonic acid (HEPES) and containing oligonucleotide ON3 as hereinbefore defined (1.2 mg). The resulting MLV's are subjected to ten liquid nitrogen-water freeze-thaw cycles and then sonicated (wavelength 6 $\mu$m) for 2 minutes to give small unilamellar vesicles (SUVs) having an average diameter of 80 to 100 nm. The resulting liposomes are purified to remove unentrapped oligonucleotide by size exclusion chromatography using a Sephadex G-150 column and a 25 mM sodium borate elution buffer.

Human lung adenocarcinoma A549 cells are implanted subcutaneously under the dorsal outer skin of nude mice. A suspension of the oligonucleotide-containing liposomes in phosphate buffered saline is administered by intravenous injection at a dosage of 0.60 mg/kg once daily beginning on day 10 after tumour cell inoculation. Tumour size is measured and tumour volume calculated on days 10, 14, 17, 21, 24 and 27 following tumour cell inoculation. The above test is repeated with the oligonucleotide-containing liposomes being administered at a dosage of 0.60 mg/kg a) every second day, b) every third day and c) once weekly, beginning on day 10 following tumour cell inoculation. The above test procedure is repeated using a solution of oligonucleotide ON3, instead of liposomes containing ON3, in phosphate buffered saline. The test results are as follows:

| Daily Administration | | |
|---|---|---|
| | Tumour Volume (cm$^3$) | |
| Days After Inoculation | ON3 | ON3 in Liposomes |
| 10 | 0.1130 | 0.1160 |
| 14 | 0.0830 | 0.0700 |
| 17 | 0.0850 | 0.0580 |
| 21 | 0.1210 | 0.0510 |
| 24 | 0.1340 | 0.0610 |
| 27 | 0.1560 | 0.0670 |

| Administration Every Second Day | | |
|---|---|---|
| | Tumour Volume (cm$^3$) | |
| Days After Inoculation | ON3 | ON3 in Liposomes |
| 10 | 0.1160 | 0.1270 |
| 14 | 0.1010 | 0.0810 |
| 17 | 0.1160 | 0.0810 |
| 21 | 0.1690 | 0.0820 |
| 24 | 0.2540 | 0.0920 |
| 27 | 0.3300 | 0.1090 |

| Administration Every Third Day | | |
|---|---|---|
| | Tumour Volume (cm$^3$) | |
| Days After Inoculation | ON3 | ON3 in Liposomes |
| 10 | 0.1230 | 0.1130 |
| 14 | 0.1150 | 0.0700 |
| 17 | 0.1750 | 0.0700 |
| 21 | 0.2260 | 0.0710 |

-continued

Administration Every Third Day

| Days After Inoculation | Tumour Volume (cm³) ON3 | ON3 in Liposomes |
|---|---|---|
| 24 | 0.4290 | 0.0970 |
| 27 | 0.6650 | 0.1210 |

Weekly Administration

| Days After Inoculation | Tumour Volume (cm³) ON3 | ON3 in Liposomes |
|---|---|---|
| 10 | 0.1300 | 0.1230 |
| 14 | 0.1510 | 0.0980 |
| 17 | 0.2460 | 0.1310 |
| 21 | 0.3980 | 0.2110 |
| 24 | 0.7090 | 0.3460 |
| 27 | 1.0660 | 0.5010 |

EXAMPLE 2

Liposomes containing entrapped oligonucleotide ON3 are prepared using the procedure described in Example 1, but replacing the lipid mixture used in that Example by hydrogenated phosphatidylinositol, distearoyl phosphatidylcholine and cholesterol in a molar ratio of 1:10:5.

The ability of the liposomes to inhibit uptake of oligonucleotide ON3 by murine macrophage-like J774 cells is tested using the procedure of Namba et al, 1992, Life Sciences, 50, 1773–1779, with minor modifications. After an incubation period of 360 minutes, the uptake of ON3 by the J774 cells is 0.583%. When the procedure is repeated, replacing the liposomes by a solution of ON3 in phosphate buffered saline, the uptake of ON3 by the J774 cells is 8.714%.

EXAMPLE 3

Liposomes containing entrapped oligonucleotide ON3 are prepared using the procedure described in Example 1, but replacing the lipid mixture used in that Example by ganglioside $GM_1$ (ex Sigma Chemicals), distearoyl phosphatidylcholine and cholesterol in a molar ratio of 1:10:5 and using a 2:1 (by volume) mixture of methanol:chloroform, instead of chloroform alone, as the solvent for the lipids. The liposomes are tested as in Example 2: after an incubation period of 360 minutes, the uptake of ON3 by J774 cells is 0.422%.

What is claimed is:

1. A pharmaceutical composition comprising (A) an oligonucleotide 8 to 50 nucleotides in length, which is targeted to mRNA encoding human raf and inhibits raf expression, entrapped in (B) sterically stabilised liposomes.

2. The composition according to claim 1, in which at least one nucleotide of the oligonucleotide (A) is modified at the 2' position of the sugar moiety.

3. The composition according to claim 1, in which the oligonucleotide (A) is a chimeric oligonucleotide which contains a first region having at least one nucleotide modified to enhance target affinity and a second region which is a substrate for RNAse H.

4. The composition according to claim 3, in which a nucleotide modified to enhance target affinity is modified at the 2' position of the sugar moiety.

5. The composition according to claim 2, in which the modified nucleotide has an alkoxy, alkoxyalkoxy or fluoro substituent at the 2' position.

6. The composition according to claim 3, in which the oligonucleotide (A) is a chimeric oligonucleotide and the region which is a substrate for RNAse H comprises at least one 2'-deoxynucleotide.

7. The composition according to claim 1, in which the oligonucleotide (A) has at least one phosphorothioate linkage.

8. The composition according to claim 1, in which, in the oligonucleotide (A), all nucleotides are 2'-deoxynucleotides and all backbone linkages are phosphorothioate linkages.

9. The composition according to claim 1, in which the oligonucleotide (A) is a chimeric oligonucleotide having one or more regions with 2'-deoxynucleotides and one or more regions with 2'-alkoxyalkoxynucleotides.

10. The composition according to claim 9, in which the 2'-alkoxyalkoxynucleotides are 2'-methoxyethoxynucleotides.

11. The composition according to claim 9, in which the one or more regions with 2'-deoxynucleotides have phosphorothioate backbone linkages and the one or more regions with 2'-alkoxyalkoxynucleotides have phosphodiester backbone linkages.

12. The composition according to claim 9, in which the oligonucleotide (A) comprises a region of 2'-deoxynucleotides between two regions of 2'-alkoxyalkoxynucleotides.

13. The composition according to claim 1, wherein the oligonucleotide (A) is targeted to mRNA encoding human A-raf.

14. The composition according to claim 1, in which the oligonucleotide (A) is targeted to mRNA encoding human c-raf.

15. The composition according to claim 14, in which the oligonucleotide (A) is targeted to a translation initiation site, 3' untranslated region or 5' untranslated region of mRNA encoding human c-raf.

16. The composition according to claim 1 in which the oligonucleotide (A) comprises a nucleotide sequence

```
GCTCCATTGATGCAGCTTAA      (SEQ ID NO:1)

or

GATGCAGCTTAAACAATTCT      (SEQ ID NO:2)

or
```

-continued
```
TCCCGCCTGTGACATGCATT      (SEQ ID NO:3)

or

GTCTGGCGCTGCACCACTCT      (SEQ ID NO:4)

or

CGCTCCTCCTCCCCGCGGCG      (SEQ ID NO:5)

or

TCCTCCTCCCCGCGGCGGGT      (SEQ ID NO:6)

or

CTCGCCCGCTCCTCCTCCCC      (SEQ ID NO:7)

or

CTGGCTTCTCCTCCTCCCCT      (SEQ ID NO:8)

or

CGGGAGGCGGTCACATTCGG      (SEQ ID NO:9)

or

TCTGGCGCTGCACCACTCTC      (SEQ ID NO:10)

or

TTCTCGCCCGCTCCTCCTCC      (SEQ ID NO:11)

or

TTCTCCTCCTCCCCTGGCAG      (SEQ ID NO:12)

or

CCTGCTGGCTTCTCCTCCTC      (SEQ ID NO:13).
```

17. The composition according to claim 1, in which the liposomes (B) comprise at least one underivatised vesicle-forming lipid and at least one vesicle-forming lipid which is derivatised with a hydrophilic polymer.

18. The composition according to claim 17, in which the hydrophilic polymer is a polyethyleneglycol.

19. The composition according to claim 17, in which the derivatised lipid is a phospholipid having an amino group.

20. The composition according to claim 19, in which the hydrophilic polymer is attached to the phospholipid through a carbamate linkage.

21. The composition according to claim 19, in which the amino-containing phospholipid is a phosphatidylethanolamine.

22. The composition according to claim 21, in which the amino-containing phospholipid is distearoyl phosphatidylethanolamine.

23. The composition according to claim 17, in which the derivatised lipid comprises 1–20 mole % of the total lipid content of the liposomes.

24. The composition according to claim 17, in which the underivatised lipid is a lipid having two hydrocarbon chains and a polar head group and/or a sterol.

25. The composition according to claim 24, in which the lipid having two hydrocarbon chains and a polar head group is a phosphatidylcholine.

26. The composition according to claim 25, in which the phosphatidylcholine is distearoyl phosphatidylcholine.

27. The composition according to claim 24, in which the sterol is cholesterol.

28. The composition according to claim 17, in which the liposomes comprise 4–10 mol % derivatised lipid, 40–80 mol % underivatised lipid and 20–50 mol % sterol.

29. The composition according to claim 28, in which the molar ratio of derivatised lipid: underivatised lipid: sterol is 1:10:5.

30. The composition according to claim 1, in which the liposomes (B) comprise (i) a glycolipid together with (ii) a vesicle-forming phospholipid or sphingolipid or mixture thereof and, optionally, (iii) a sterol and/or an acylglycerol lipid.

31. The composition according to claim 30, in which the glycolipid is a negatively charged glycolipid.

32. The composition according to claim 31, in which the liposomes comprise (i) a negatively charged glycolipid together with (ii) a vesicle-forming phospholipid and/or sphingolipid and (iii) a sterol or acylglycerol lipid.

33. The composition according to claim 31, in which the glycolipid is ganglioside $GM_1$ or hydrogenated phosphatidylinositol.

34. The composition according to claim 30, in which the vesicle-forming phospholipid is a phosphatidylcholine or a phosphatidylethanolamine.

35. The composition according to claim 34, in which the phospholipid is distearoyl phosphatidylcholine or dioleoyl phosphatidylethanolamine.

36. The composition according to claim 30, in which the sphingolipid is sphingomyelin.

37. The composition according to claim 30, in which the acylglycerol lipid has two fatty acid acyl groups each having at least 12 carbon atoms and one acyl group of formula $R^1CO-$, where $R^1$ is a residue, containing up to 10 carbon atoms, of a monocarboxylic acid of formula $R^1COOH$ after removal of the —COOH group, or of formula $OC-R^2-COOH$ where $R^2$ is a residue, containing up to 10 carbon atoms, of a dicarboxylic acid of formula $HOOC-R^2-COOH$ after removal of both —COOH groups.

38. The composition according to claim 37, in which the acylglycerol is 1,2-dipalmitoyl-sn-3-succinyl glycerol.

39. The composition according to claim 30, in which the liposomes comprise 2 to 20 mol % of the glycolipid, 40 to 80 mol % of the phospholipid, sphingolipid or mixture thereof and 10 to 50 mol % of the sterol or 10 to 30 mol % of the acylglycerol.

40. The composition according to claim 39, in which the liposomes comprise 4 to 10 mol % of the glycolipid, 60 to 80 mol % of the phospholipid, sphingolipid or mixture thereof and 20 to 40 mol % of the sterol or 10 to 30 mol % of the acylglycerol.

41. The composition according to claim 1, in which the liposomes have an average particle size of 50 to 200 nm.

42. The composition according to claim 41, in which the liposomes have an average particle size of 80 to 120 nm.

43. A method of inhibiting the expression of human raf which comprises contacting tissues or cells which express human raf with a composition according to claim 1.

44. A method of treating mammalian cancer which comprises administering a composition according to claim 1 to a mammal in need of such treatment.

* * * * *